United States Patent [19]

Fukuoka et al.

[11] Patent Number: 5,104,992

[45] Date of Patent: Apr. 14, 1992

[54] METHOD OF PREPARING 2-PHENYL BENEZOTHRIAZOLES

[75] Inventors: Naohiko Fukuoka, Kobe; Kazunobu Kubota, Tatsuno; Kunitoshi Iguchi, Osaka, all of Japan

[73] Assignee: Chemipro Kasei Kaisha, Ltd., Hyogo, Japan

[21] Appl. No.: 504,101

[22] Filed: Apr. 2, 1990

Related U.S. Application Data

[63] Continuation of Ser. No. 321,576, Mar. 9, 1989, abandoned.

[30] Foreign Application Priority Data

Jan. 31, 1989 [JP] Japan .................................. 1-22224

[51] Int. Cl.$^5$ .............................................. C07D 249/18
[52] U.S. Cl. ................................. 548/260; 548/259; 548/261
[58] Field of Search ................. 548/257, 259, 250, 261

[56] References Cited

U.S. PATENT DOCUMENTS

| | | | |
|---|---|---|---|
| 3,978,074 | 8/1976 | Jancis | 548/259 |
| 4,086,242 | 4/1978 | Diehl | 71/92 |
| 4,943,637 | 7/1990 | Seino et al. | 548/260 |
| 4,999,433 | 3/1991 | Prestel | 548/260 |

FOREIGN PATENT DOCUMENTS

| | | | |
|---|---|---|---|
| 1073463 | 3/1980 | Canada | 548/260 |
| 0363318 | 4/1990 | European Pat. Off. | 548/260 |

OTHER PUBLICATIONS

CA 109 (19): 170439m abstracting JP 072682 1988.
Kawaken Chem. Abstr. vol. 88 Entry 105346n Abstracting JP 77-113973 (1977).
CA 102 (5): 45959k abstracting JP170172 1984.
CA 88 (26): 197149b abstracting JP 133076 1977.
CA 88 (21): 152408u abstracting JP 133973 1977.
CA 88 (15): 105347p abstracting JP 113974 1977.
CA 106 (21): 176394e abstracting JP 215378 1986.
CA 110 (6): 47417w abstracting JP 186886 1988.

*Primary Examiner*—Donald G. Davis
*Attorney, Agent, or Firm*—Felfe & Lynch

[57] ABSTRACT

A method of preparing 2-phenylbenzotriazoles expressed by Formula I:

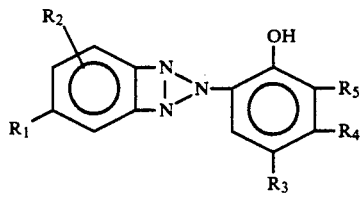

(wherein $R_1$ denotes a hydrogen or chlorine atom, a lower alkyl group having 1 to 4 carbon atoms, a lower alkoxyl group having 1 to 4 carbon atoms, a carboxyl group or a sulfonic acid group; $R_2$ denotes a hydrogen or chlorine atom, a lower alkyl group having 1 to 4 carbon atoms or a lower alkoxyl group having 1 to 4 carbon atoms; $R_3$ denotes a hydrogen or chlorine atom, an alkyl group having 1 to 12 carbon atoms, a lower alkoxy group having 1 to 4 carbon atoms, a phenyl group, a phenyl group substituted by an alkyl group having 1 to 8 carbon atoms, a phenoxy group or a phenylalkyl group with an alkyl part having 1 to 4 carbon atoms; $R_4$ denotes a hydrogen or chlorine atom, a hydroxyl group or an alkoxyl group having 1 to 4 carbon atoms; and $R_5$ denotes a hydrogen atom, an alkyl group having 1 to 12 carbon atoms or a phenylalkyl group with an alkyl part having 1 to 4 carbon atoms) comprises reducing with hydrogen 2-phenylbenzotriazole-N-oxides expressed by Formula II:

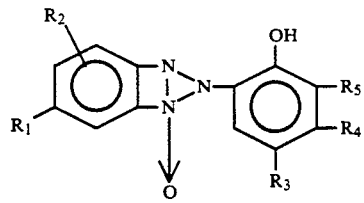

(wherein $R_1$, $R_2$, $R_3$, $R_4$ and $R_5$ each denotes the same as in Formula I).

7 Claims, No Drawings

METHOD OF PREPARING 2-PHENYL BENEZOTHRIAZOLES

This application is a continuation of application Ser. No. 321,576 filed Mar. 9, 1989, now abandoned.

BACKGROUND OF THE INVENTION

1. Field of the Invention

The present invention relates to a method of preparing 2-phenyl benzotriazoles which are useful as ultraviolet ray absorbers in plastics, paints, oils and so on, and which are expressed by the following formula I:

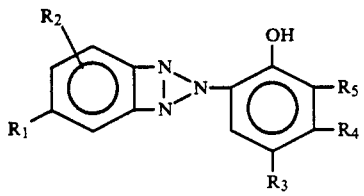

(wherein $R_1$ denotes a hydrogen atom, a chlorine atom, a lower alkyl group having 1 to 4 carbon atoms, a lower alkoxyl group having 1 to 4 carbon atoms, a carboxyl group or a sulfonic acid group; $R_2$ denotes a hydrogen or chlorine atom, a lower alkyl group having 1 to 4 carbon atoms or a lower alkoxyl group having 1 to 4 carbon atoms; $R_3$ denotes a hydrogen or chlorine atom, an alkyl group having 1 to 12 carbon atoms, a lower alkoxyl group having 1 to 4 carbon atoms, a phenyl group, a phenyl group substituted by an alkyl group having 1 to 8 carbon atoms, phenoxy group or a phenylalkyl group with an alkyl part having 1 to 4 carbon atoms; $R_4$ denotes a hydrogen or chlorine atom, a hydroxyl group or an alkoxyl group having 1 to 4 carbon atoms; and $R_5$ denotes a hydrogen atom, an alkyl group having 1 to 12 carbon atoms or a phenylalkyl group with an alkyl part having 1 to 4 carbon atoms).

The present invention particularly relates to a method for preparing 2-phenyl benzotriazoles expressed by Formula I comprising reduction with hydrogen of 2-phenyl benzotriazole-N-oxides expressed by the following formula II:

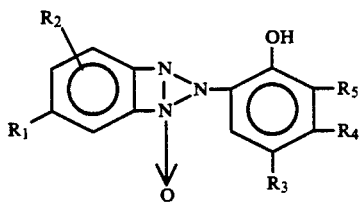

(wherein $R_1$, $R_2$, $R_3$, $R_4$ and $R_5$ each denote the same as in Formula I).

2. Description of the Prior Art

Such 2-phenylbenzotriazoles are generally produced by chemical or electrolytic reduction of o-nitrohydroxy azobenzenes expressed by the following formula III:

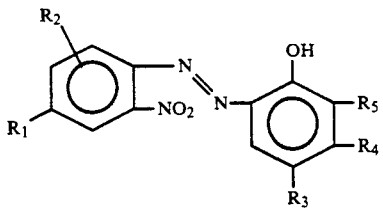

(wherein $R_1$, $R_2$, $R_3$, $R_4$ and $R_5$ each denote the same as in Formula I). Each of these conventional methods, however, has its own advantages and disadvantages, and is not always completely satisfactory. For example, Japanese Patent Publication No. 5934/1962 and U.S. Pat. No. 3,773,751 disclose a method of preparing 2-phenylbenzotriazoles in a good yield by chemically reducing o-nitroazobenzenes with zinc powder in an alcoholic sodium hydroxide solution. Such a sodium hydroxide-zinc system, however, involves the problem that it produces zinc sludge which causes contamination of waste water, and the disadvantage that the waste produced cannot easily be disposed of.

U.S. Pat. No. 2,362,988 discloses a method which uses as a reductant ammonium sulfide, an alkali sulfide, a zinc-ammonia system, a hydrogen sulfide-sodium system or a zinc-hydrochloric acid system. This method, however, has the disadvantages that a large amount of sulfite or zinc salts is produced, resulting in problems with respect to waste water contamination and difficulty of waste disposal, Japanese Patent Laid-Open No. 133076/1981 (Chem. Abstr. 88 197149b) discloses a method which uses as a catalyst an aromatic dihydroxy compound or a quinone compound and which also requires as a reductant zinc, ammonium sulfide, an alkali metal sulfide, hydrosulfite or hydrazine. This method also has the above-described problem with respect to waste water containing metals, as well as involving problems with respect to the generation of poisonous gases from sulfide reductants and the toxicity of hydrazine itself.

Japanese Patent Laid Nos. 113974/1977 and 113973/1977 (Chem. Abstr. 88 152408u and 105347p respectively) disclose a method of preparing 2-phenylbenzotriazoles in a good yield by reducing the corresponding o-nitroazobenzenes with hydrogen in the presence of a hydrogenation catalyst and a basic substance. As a result of supplementary studies, however, it has been found that many kinds of impurities are produced in small amounts and cannot be removed by washing the reaction product with methanol and then recrystallizing it with ethanol. This method therefore has the problem that the 2-phenylbenzotriazoles produced by this method are inferior to those available at present in terms of both quality and cost.

Japanese Patent Laid-Open No. 170172/1984 (Chem. Abstr. 102 45959k) and Japanese Patent Laid-Open No. 72682/1998 (U.S. Pat. No. 4,943,637) which are related to this application disclose methods of reducing o-nitroazobenzene derivatives expressed by Formula I with alcohols in basic catalysts using quinones and aromatic ketones, respectively.

These methods are excellent methods which can resolve the problems described above with respect to air pollution and waste water contamination, but they still involve the following disadvantages:

The method disclosed in Japanese Patent Laid-Open No. 72682/1988 which uses aromatic ketones as catalysts exhibits a good yield with the expensive catalyst used but is unsuitable for large-scale production on an industrial scale because heat is rapidly generated during the course of the reaction. The method disclosed in Japanese Patent Laid-Open No. 170172/1984 which uses quinones as catalysts exhibits a relatively good yield but higher costs are involved because the quinones used as catalysts deteriorate and cannot be recovered. This method is also unsuitable for use as an additive in colorless plastics because the resulting products would become strongly tinged with yellow. This tendency is particularly strong in the case where $R_3$ in Formula II is an alkyl group and $R_1$, $R_2$, $R_4$ and $R_5$ are each a hydrogen atom.

The applicant has proposed a method of preparing 2-phenylbenzotriazoles expressed by Formula I by reducing 2-phenylbenzotriazole-N-oxides of Formula II or o-nitroazobenzenes of Formula III in the following manner:

(1) reduction with an aldehyde in the presence of an aromatic ketone compound and a base (Japanese Patent-Laid Open No. 21537/1986, Chem. Abstr. 106 176394c);

(2) reduction with a primary or secondary alcohol in the presence of a catalyst comprising an aromatic ketone compound together with a basic compound (Japanese Patent Laid-Open No. 72683/1988, U.S. Pat. No. 4,780,541); or (3) electrolytic reduction in the presence of an alkali metal hydroxide in water or a mixture of water and, alcohol (Japanese Patent Laid-Open No. 186886/1988, Chem. Abstr. 47417u ).

The applicant has also proposed a method for preparing 2-phenylbenzotriazole expressed by the above-described Formula I by reducing the 2-phenylbenzotriazole-N-oxides with an aldehyde in the presence of a catalyst comprising an aromatic ketone compound with a basic compound (Japanese Patent Laid-Open No. 215379/1986, U.S. Pat. No. 4,780,541).

SUMMARY OF THE INVENTION

It is an object of the present invention to provide a novel method for preparing 2-phenylbenzotriazoles.

It is another object of the present invention to provide reaction products which allow 2-phenylbenzotriazoles to be easily isolated and purified as target products by simple reduction with hydrogen.

As a result of various investigations conducted by the inventors with a view to resolving the above-described problems, it has been found that 2-phenylbenzotriazoles can be produced in a good yield, with only a small amount of impurities being produced, by using as starting materials 2-phenylbenzotriazole-N-oxides. The results compare favorably with a method that employs o-nitroazobenzenes as starting materials.

That is, the present invention relates to a method of preparing 2-phenylbenzotriazoles expressed by Formula I by reducing 2-phenylbenzotriazole-N-oxides expressed by Formula II with hydrogen. The present invention particularly relates to a method of preparing 2-phenylbenzotriazoles by contact-reducing 2-phenylbenzotriazole-N-oxides with hydrogen in the presence of a hydrogenation catalyst and a basic substance in a solvent. More particularly, the present invention relates to a method in which the reduction is effected in a mixed solvent comprising water and one or more organic solvents selected from the group comprising aromatic hydrocarbons, alcohols, cyclic ethers.

The outline of an example of the present invention is given below.

A 2-phenylbenzotriazole-N-oxide which is the chosen starting material is dissolved in a solvent contained in a reaction vessel into which a hydrogenation catalyst and a basic substance are then placed. After the air in the reaction vessel has been replaced by hydrogen, a given amount of hydrogen is charged into the reaction vessel, and the reaction is then allowed to proceed under atmospheric pressure or a given pressure at a temperature of room temperature to 170° C. under agitation. After the reaction has been completed, the catalyst is filtered off, the solvent layer is washed with water, and the solvent is distilled off. The crude product is then purified by recrystallization to obtain the corresponding 2-phenylbenzotriazole as a pure product.

Examples of compounds expressed by Formula II that may be used as raw materials in the present invention include the following:

2-(2'-hydroxy-3'-t-butyl-5'-methylphenyl)-5-chlorobenzotriazole-N-oxide 2-(2'-hydroxy-3',5'-di-t-butylphenyl)-5-chlorobenzotriazole-N-oxide 2-(2'-hydroxy-3',5'-di-t-amylphenyl)benzotriazole-N-oxide 2-(2'-hydroxy-5'-methylphenyl)benzotriazole-N-oxide 2-(2'-hydroxy-5'-t-octylphenyl)benzotriazole-N-oxide 2-(2'-hydroxy-5'-t-butylphenyl)benzotriazole-N-oxide 2-(2'-hydroxy-3',5'-di-t-butylphenyl)benzotriazole-N-oxide 2-(2'-hydroxy-3'-t-butyl-5'-methylphenyl)benzotriazole-N-oxide 2-(2',4'-dihydroxyphenyl)-5-chlorobenzotriazole-N-oxide 2-(2',4'-dihydroxyphenyl)benzotriazole-N-oxide 2-(2'-hydroxy-4'-methoxyphenyl)benzotriazole-N-oxide 2-[2'-hydroxy-3,5-di($\alpha,\alpha$-dimethylbenzyl)phenyl]benzotriazole-N-oxide 2-(2'-hydroxy-3'-$\alpha$-methylbenzyl-5'-methylphenyl)-benzotriazole-N-oxide These N-oxides expressed by Formula II can be formed by various reduction methods using as raw materials o-nitroazobenzenes expressed by Formula III.

Examples of o-nitroazobenzene derivatives expressed by Formula III include the following:

2-nitro-4-chloro-2'-hydroxy-3'-t-butyl-5'-methylazobenzene 2-nitro-2'-hydroxy-5-methylazobenzene 2-nitro-2'-hydroxy-5'-t-octylazobenzene 2-nitro-2'-hydroxy-5'-t-butylazobenzene 2-nitro-4-chloro-2'-hydroxy-3',5'-di-t-butylazobenzene 2-nitro-2'-hydroxy-3',5'-di-t-amylazobenzene 2-nitro-2'-hydroxy-3',5'-di-t-butylazobenzene 2-nitro-2'-hydroxy-3'-t-butyl-5'-methylazobenzene 2-nitro-2',4'-dihydroxyazobenzene 2-nitro-4-chloro-2',4'-dihydroxyazobenzene 2-nitro-2'-hydroxy-4'-methoxyazobenzene 2-nitro-4-chloro-2'-hydroxy-3',5'-di-t-amylazobenzene 2-nitro-2'-hydroxy-5'-t-amylazobenzene 2-nitro-4-chloro-2'-hydroxy-5'-t-amylazobenzene 2-nitro-2'-hydroxy-3',5'-di($\alpha,\alpha$-dimethylbenzyl)azobenzene 2-nitro-4-chloro-2'-hydroxy-3',5'-di-($\alpha,\alpha$-dimethylbenzyl)azobenzene 2-nitro-2'-hydroxy-3'-α-methylbenzyl-5'-methylazobenzene
2-nitro-4-chloro-2'-hydroxy-3'-α-methylbenzyl-5'-methylazobenzene
2-nitro-2'-hydroxy-5'-n-dodecylazobenzene
2-nitro-4-chloro-2'-hydroxy-5'-n-dodecylazobenzene
2-nitro-2'-hydroxy-3',5'-di-t-octylazobenzene
2-nitro-4-chloro-2'-hydroxy-3',5'-di-t-octylazobenzene
2-nitro-4-chloro-2'-hydroxy-5'-t-octylazobenzene
2-nitro-4-methyl-2'-hydroxy-5'-methylazobenzene
2-nitro-4-methyl-2'-hydroxy-3'-t-butyl-5-methylazobenzene
2-nitro-4-n-butyl-2'-hydroxy-3',5'-di-t-butylazobenzene
2-nitro-4-n-butyl-2'-hydroxy-3'-sec-butyl-5'-t-butylazobenzene
2-nitro-4-t-butyl-2'-hydroxy-3'-sec-butyl-5'-t-butylazobenzene
2-nitro-4,6-dichloro-2'-hydroxy-5'-t-butylazobenzene
2-nitro-4,6-dichloro-2'-hydroxy-3',5'-di-t-butylazobenzene
2-nitro-4-carboxy-2'-hydroxy-5-methylazobenzene Examples of hydrogenation catalysts that may be used in the present invention include Raney nickel, platinum oxide, platinum carbon, palladium carbon, ruthenium carbon, rhodium carbon and the like.

Examples of basic substances that may be used as additives in the present invention include hydroxides and carbonates of alkali metals; hydroxides and carbonates of alkali earth metals; alkyl amines such as methylamine, ethylamine, propylamine, dimethylamine, diethylamine, dibutylamine, triethylamine and tributylamine; polyalkylenepolyamines such as diethylenetriamine, triethylenetetramine, dipropylenetriamine and tripropylenetetramine; alkanolamines such as monoethanolamine, monopropanolamine, diethanolamine, dipropanolamine, triethanolamine and tripropanolamine; aromatic amines such as aniline, tolylamine and methylcyclohexylamine; heterocyclic amines such as pyridine, piperazine, triethylenediamine, diazabicyclononene and diazabicycloundecene.

Examples of organic solvents that may be used in the present invention include aromatic hydrocarbons such as benzene, toluene, xylene and the like; alcohols such as methanol, ethanol, n-propanol, n-butanol, isobutanol, n-amyl alcohol, isoamyl alcohol, sec-butanol, isopropyl alcohol and the like; and cyclic ethers such as dioxane, tetrahydrofuran and the like.

Although the amount of the hydrogenation catalyst used in the present invention depends upon the type thereof, it is generally 20 wt % or less, preferably about 0.1 wt % or more, of the weight of the N-oxide compound expressed by Formula II. The amount of the basic substance used is preferably 0 to 30 wt % of the weight of the N-oxide compound expressed by Formula II. The amount of the reaction solvent used may be about 40 times or less, preferably about twice or more, the weight of the substance to be reduced expressed by Formula II. The amount of the water added is 0.2 to 35 times the weight of the substance to be reduced. The mixing ratio between the organic solvent and water is generally 1:2 to 50:1 by volume, preferably 2:1 to 30:1 by volume. The reaction temperature is room temperature to about 170° C., preferably about 15° to 70° C. The pressure of hydrogen is normal pressure to about 20 kg/cm$^2$.

Typical of benzotriazole compounds obtained in the present invention are expressed by Formula I. Examples of such compounds include the following:

2-(2'-hydroxy-3'-t-butyl-5'-methylphenyl)-5-chlorobenzotriazole
2-(2'-hydroxy-3',5'-di-t-butylphenyl)-5-chlorobenzotriazole
2-(2'-hydroxy-3',5'-di-t-amylphenyl)benzotriazole
2-(2'-hydroxy-5'-methylphenyl)benzotriazole
2-(2'-hydroxy-5'-t-butylphenyl)benzotriazole
2-(2'-hydroxy-5'-t-octylphenyl)benzotriazole
2-(2'-hydroxy-3',5'-di-t-butylphenyl)benzotriazole
2-(2'-hydroxy-3'-t-butyl-5'-methylphenyl)benzotriazole
2-(2',4'-dihydroxyphenyl)benzotriazole
2-(2'-hydroxy-4'-methoxyphenyl)benzotriazole
2-[2'-hydroxy-3',5'-di(α,α-dimethylbenzyl)phenyl] benzotriazole
2-(2'-hydroxy-3'-α-methylbenzyl-5'-methylphenyl) benzotriazole In the present invention, the selection of 2-phenylbenzotriazole-N-oxides expressed by Formula II as starting materials enables 2-phenylbenzotriazoles to be produced in a good yield by reduction with hydrogen, as well as enabling the target products to be simply isolated and purified because no side-reaction takes place owing to the cleavage of amino groups and because the amount of products resulting from side-reactions is small as compared with conventional methods. As a result, benzotriazoles can be obtained as high quality target substances in high yields.

DESCRIPTION OF THE PREFERRED EMBODIMENTS

The present invention is further illustrated by the following Examples and Comparative Examples concerning preparation and usage, but should not be limited thereto.

EXAMPLE 1

33.9 g (0.1 mol) of 2-(2'-hydroxy-3',5'-di-ti-butylphenyl)benzotriazole-N-oxide, 0.125 g of 5% palladium carbon, 150 ml of a solvent mixture comprising toluene and water (ratio by volume, 4:1) and 7 g of an aqueous solution of 50% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 87.3% of 2-(2'-hydroxy-3',5'-di-t-butylphenyl)benzotriazole. The solvent was then distilled off from the filtrate, and the residual solid was crystallized using ethanol and then washed with ethanol to obtain 23.6 g of 2-(2'-hydroxy-3',5'-di-t-butylphenyl)benzotriazole (yield, 73%; melting point, 152° to 156° C.).

EXAMPLE 2

33.9 g (0.1 mol) of 2-(2'-hydroxy-3',5'-di-t-butylphenol)benzotriazole-N-oxide, 0.125 g of 5% palladium carbon, 150 ml of a solvent mixture comprising toluene and methanol (ratio by volume, 4:1) and 7 g of 99% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 83.4% of 2-(2'-hydroxy-3',5'-di-t-butylphenyl)-benzotriazole. The solvent was then distilled off from the filtrate, and the residual solid was crystallized using ethanol and then washed with ethanol to obtain 22.9 g of 2-(2'-hydroxy-3',5'-di-t-butylphenyl)benzotriazole (yield, 70.9%; melting point, 152° to 155° C.).

EXAMPLE 3

10 g (0.03 mol) of 2-(2'-hydroxy-3',5'-di-t-butylphenyl)benzotriazole-N-oxide, 100 mg of palladium carbon, 100 ml of a solvent mixture comprising toluene and water (ratio by volume, 4:1) and 3 g of 50% dimethylamine were charged into a 500-ml autoclave equipped with an agitator. After the air in the autoclave had been replaced by hydrogen, the pressure of hydrogen was set to 10 kg/cm$^2$. The temperature was increased to 50° C. under agitation, and reaction was effected at the same temperature while agitation being continued until no more hydrogen was absorbed by the mixture. After the reaction had been completed, the autoclave was cooled, and the catalyst was filtered off. When part of the filtrate was subjected to quantitative analysis using GC, it was found that the yield of 2-(2'-hydroxy-3',5'-di-t-butylphenyl)benzotriazole is 85.6%. After the solvent had been distilled off from the filtrate, the residual solid was crystallized by ethanol and then washed with ethanol to obtain 7.1 g of 2-(2'-hydroxy-3',5'-di-t-butylphenyl)benzotriazole (yield, 71%; melting point, 152° to 155° C.).

EXAMPLE 4

36.7 g (0.1 mol) of 2-(2'-hydroxy-3',5'-di-t-amylphenyl)benzotriazole-N-oxide, 0.125 g of 5% palladium carbon, 150 ml of a toluene solvent and 7 g of 50% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 93% of 2-(2'-hydroxy-3',5'-di-t-amylphenyl)-benzotriazole. The solvent was then distilled off from the filtrate, and the residual solid was crystallized using ethanol and then washed with ethanol to obtain 28.1 g of 2-(2'-hydroxy-3',5'-di-t-amylphenyl)benzotriazole (yield, 80%; melting point, 79° to 81° C.).

EXAMPLE 5

36.7 g (0.1 mol) of 2-(2'-hydroxy-3',5'-di-t-amylphenyl)benzotriazole-N-oxide, 0.125 g of 5% palladium carbon, 150 ml of a solvent mixture comprising toluene and water (ratio by volume, 4:1) and 7 g of 50% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 90.8% of 2-(2'-hydroxy-3',5'-di-t-amylphenyl)benzotriazole. The solvent was then distilled off from the filtrate, and the residual solid was crystallized using ethanol and then washed with ethanol to obtain 28 g of 2-(2'-hydroxy-3',5'-di-t-amylphenyl)benzotriazole (yield, 80%; melting point, 79° to 82° C.).

EXAMPLE 6

24.1 g (0.1 mol) of 2-(2'-hydroxy-5'-methylphenyl)-benzotriazole-N-oxide, 0.125 g of 5% palladium carbon, 150 ml of a solvent mixture comprising toluene and water (ratio by volume, 4:1) and 7 g of 50% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 89% of 2-(2'-hydroxy-5'-methylphenyl)benzotriazole. The solvent was then distilled off from the filtrate, and the residual solid was crystallized using ethanol and then washed with ethanol to obtain 18 g of 2-(2'-hydroxy-5'-methylphenyl) benzotriazole (yield, 80%; melting point, 128° to 130° C.).

EXAMPLE 7

24.1 g (0.1 mol) of 2-(2'-hydroxy-5'-methylphenyl)-benzotriazole-N-oxide, 9.6g of Raney nickel (produced by Kawaken Fine Chemical Co., Ltd.), 150 ml of a solvent mixture comprising toluene and water (ratio by volume, 4:1) and 7 g of 50% dimethylamine were charged into a 500-ml four neck flask. After the air in the flask had been replaced by nitrogen, the resultant mixture was agitated at room temperature. Hydrogen was then supplemented to allow for the amount of hydrogen absorbed by the mixture, which was then subjected to reaction until no more hydrogen was absorbed by it. After the reaction had bee completed, the catalyst was filtered off, and part of the filtrate was subjected to quantitative analysis using gas chromatography (GC). The results revealed a yield of 67% of 2-(2'-hydroxy-5'-methylphenyl)benzotriazole. The solvent was then distilled off from the filtrate, and the residual solid was crystallized using ethanol and then washed with ethanol to obtain 12.4 g of 2-(2'-hydroxy-5'-methylphenyl)benzotriazole (yield, 55%; melting point, 128° to 130° C.).

EXAMPLE 8

36.7 g (0.1 mol) of 2-(2'-hydroxy-3',5'-di-t-amylphenyl)benzotriazole-N-oxide, 0.1 g of platinum carbon, 150 ml of a toluene solvent and 7 g of 50% dimethylamine were charged into a 500-ml four neck flask. After the air in the flask had been replaced by nitrogen, the resultant mixture was agitated at room temperature. Hydrogen was then supplemented for the amount of hydrogen absorbed by the mixture, which was then subjected to reaction until no more hydrogen was absorbed by it. After the reaction had been completed, the catalyst was filtered off, and part of the filtrate was subjected to quantitative analysis using gas chromatography (GC). The results revealed a yield of 96% of 2-(2'-hydroxy-3',5'-di-t-amylphenyl)benzotriazole. The solvent was then distilled off from the filtrate, and the residual solid was crystallized using ethanol and then washed with ethanol to obtain 30.5 g of 2-(2'-hydroxy-3',5'-di-t-amylphenyl)benzotriazole (yield, 87%; melting point, 79° to 81° C.).

EXAMPLE 9

37.4 g (0.1 mol) of 2-(2'-hydroxy-3',5'-di-t-butylphenyl)-5-chlorobenzotriazole-N-oxide, 0.125 g of palladium carbon, 300 ml of a solvent mixture comprising toluene, 2-butanol and water (ratio by volume of 10:7:10) and 5 g of 50% dimethylamine were charged into a 500- ml stainless autoclave equipped with an agitator. After the air in the autoclave had been replaced by hydrogen, the pressure of hydrogen was set to 10 kg/cm$^2$. The temperature of the resultant mixture was increased to 60° C. under agitation, and reaction was been effected while agitation being continued until no more hydrogen was absorbed by the mixture. After the reaction had been completed, the autoclave was cooled, and the catalyst was filtered off. After most part of the solvent had been distilled off from the filtrate, the residual solid was washed with ethanol and dried to obtain 30.4 g of 2-(2'-hydroxy-3',5'-di-t-butylphenyl)-5-chlorobenzotriazole as a target substance (yield, 85.0%; melting point, 153° to 155° C.).

EXAMPLE 10

37.4 g (0.1 mol) of 2-(2'-hydroxy-3',5'-di-t-butylphenyl)-5-chlorobenzotriazole-N-oxide, 0.25 g of Raney nickel catalyst, 150 ml of toluene, 100 ml of 2-butanol and 0.5 g of 1,5-diazabicyclo[5.4.0]undecene were charged into a 500-ml stainless autoclave equipped with an agitator. After the air in the autoclave had been replaced by nitrogen, hydrogen was charged to a pressure of 8 kg/cm$^2$. The temperature of the resultant mixture was increased to 60° C. under agitation, and reaction was been effected while agitation being continued until no hydrogen gas was absorbed by the mixture. After the reaction had been completed, after treatment was performed in the same way as that employed in Example 9 to obtain 28.2 g of 2-(2'-hydroxy-3',5'-di-t-butylphenyl)-5-chlorobenzotriazole as a target substance (yield, 79%; melting point, 153° to 155° C.).

EXAMPLE 11

33.2 g (0.1 mol) of 2-(2'-hydroxy-3'-t-butyl-5'-methylphenyl)-5-chlorobenzotriazole-N-oxide, 0.125 g of palladium carbon, 300 ml of a solvent mixture comprising toluene, butanol and water (ratio by volume of 1:1:1) and 5 g 50% dimethylamine were charged into a 500-ml stainless autoclave equipped with an agitator. After the air in the autoclave had been replaced by hydrogen, the pressure of hydrogen was set to 10 kg/cm$^2$. The temperature of the resultant mixture was increased to 50° C. under agitation, and agitation was continued until no more hydrogen gas was absorbed by the mixture. The pressure of hydrogen was always kept at 8 to 10 kg/cm$^2$ during the reaction. After the reaction had been completed, the autoclave was cooled, and the catalyst was filtered off. The most part of solvent was distilled off, and the residual solid was washed with isopropyl alcohol and then dried to obtain 27.2 g of 2-(2'-hydroxy-3'-t-butyl-5'-methylphenyl)-5-chlorobenzotriazole as a target substance (yield, 86.2%; melting point, 138° to 140° C.).

EXAMPLE 12

36.7 g (0.1 mol) of 2-(2'-hydroxy-3',5'-di-t-amylphenyl)benzotriazole-N-oxide, 150 ml of water, 8 g (0.2 mol) of caustic soda and 5 g of Raney nickel were charged into a 500-ml stainless autoclave equipped with an agitator. After the air in the autoclave had been replaced by hydrogen, the pressure of hydrogen was set to 10 kg/cm$^2$. The temperature of the resultant mixture was increased under agitation to 90° C. at which the mixture was then subjected to reaction for 8 hours until the absorption of hydrogen was stopped. After the reaction had been completed, the autoclave was cooled, and the catalyst was filtered off. The filtrate was then allowed to stand to separate an upper toluene layer. Most part of toluene layer was distilled off, and the resultant residual solid was crystallized from IPA and then dried to obtain 31.7 g of 2-(2'-hydroxy-3',5'-di-t-amylphenyl)benzotriazole (yield, 90.3%; melting point, 78° to 80° C.).

EXAMPLE 13

33.9 (0.1 mol) of 2-(2'-hydroxy-3',5'-di-t-butylphenyl)benzotriazole-N-oxide, 100 ml of toluene, 100 ml of isopropyl alcohol (IPA), 100 ml of water, 8.3 g of caustic soda and 5 g of Raney nickel were charged into a 500-ml stainless autoclave equipped with an agitator. After the air in the autoclave had been replaced by hydrogen, the pressure of hydrogen was set to 10 kg/cm$^2$. The temperature of the resultant mixture was increased under agitation to 95° C. at which the mixture was then subjected to reaction for 12 hours until the absorption of hydrogen was stopped.

After the reaction had been completed, after treatment was performed in the same way as that in Example 12 to obtain 23.7 g of 2-(2'-hydroxy-3',5'-di-t-butylphenyl)benzotriazole (yield, 73.3%; melting point, 150° to 152° C.).

EXAMPLE 14

37.4 g (0.1 mol) of 2-(2'-hydroxy-3',5'-di-t-butylphenyl)-5-chlorobenzotriazole-N-oxide, 100 ml of toluene, 60 ml of 2-butanol, 120 ml of water, 7 g of tributylamine and 5 g of Raney nickel were charged into a 500-ml stainless autoclave equipped with an agitator. After the air in the autoclave had been replaced by hydrogen, the pressure of hydrogen was set to 10 kg/cm$^2$. The temperature of the resultant mixture was increased under agitation to 65° C. at which the mixture was then subjected to reaction for 7 hours until the absorption of hydrogen was stopped. After the reaction had been completed, the autoclave was cooled, and the catalyst was filtered off. After the toluene layer had been separated, most part of toluene was distilled off, and the residual solid was washed with ethanol and then dried to obtain 28.3 g of 2-(2'-hydroxy-3',5'-di-t-butylphenyl)-5-chlorobenzotriazole (yield, 79.2%; melting point, 152° to 154° C.).

What we claim is:

1. A method for preparing 2-phenylbenzotriazoles of Formula I:

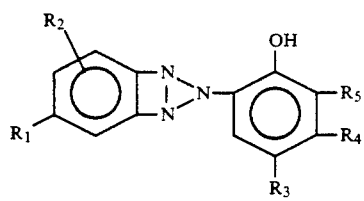

wherein $R_1$ is hydrogen or chlorine, a $C_1$-$C_4$ alkyl, a $C_1$-$C_4$ alkoxyl, a carboxyl group or a sulfonic acid group;

$R_2$ is hydrogen or chlorine, a $C_1$-$C_4$ alkyl, a $C_1$-$C_4$ alkoxyl;

$R_3$ is hydrogen or chlorine, $C_1$-$C_{12}$ alkyl, a $C_1$-$C_4$ alkoxy, a phenyl group, a phenyl group substituted by a $C_1$-$C_8$ alkyl, a phenoxy group or a phenylalkyl group with a $C_1$-$C_4$ alkyl;

$R_4$ is hydrogen or chlorine, a hydroxyl group or $C_1$-$C_4$ alkoxyl; and $R_5$ is hydrogen, a $C_1$-$C_{12}$ alkyl or a phenylalkyl group with a $C_1$-$C_4$ alkyl consisting essentially of reducing with hydrogen a starting material consisting of 2-phenylbenzotriazole-N-oxides of Formula II:

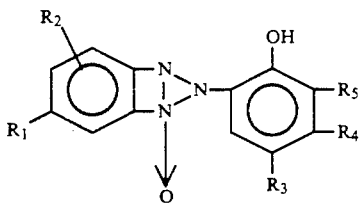

wherein $R_1$, $R_2$, $R_3$, $R_4$ and $R_5$ each denotes the same as in said Formula in the presence of a hydrogenation catalyst consisting of Raney Nickel or Palladium carbon, a basic substance selected from the group consisting of alkyl amines, polyalkylenepolyamines, alkanolamines, aromatic amines and heterocyclic non-aromatic amines and a solvent, provided that at least one of $R_1$-$R_4$ is chlorine.

2. The method of claim 1, consisting essentially of effecting the reduction in one or more solvents selected from the group consisting of aromatic hydrocarbons, alcohols and cyclic ethers.

3. The method of claim 1, consisting essentially of effecting the reduction in a solvent mixture of water and an organic solvent selected from the group consisting of aromatic hydrocarbons, alcohols and cyclic ethers.

4. The method of claim 3, consisting essentially of effecting the reduction wherein the mixing ratio between said organic solvent and said water is 1:2 to 50:1 by volume.

5. The method of claims 1 or 2, consisting essentially of effecting said reduction at the pressure of hydrogen in a range of normal pressure to 20 kg/cm² in the presence of a hydrogenation catalyst and a basic substance.

6. The method of claims 1 or 2, consisting essentially of effecting said reduction in a temperature range of room temperature to 170° C.

7. The method of claim 1, consisting essentially of using as the amount of said basic substance at least 0.1% by weight of the 2-phenylbenzotriazole-N-oxide as the starting material.

* * * * *

UNITED STATES PATENT AND TRADEMARK OFFICE
CERTIFICATE OF CORRECTION

PATENT NO. : 5,104,992
DATED : April 14, 1992
INVENTOR(S) : Naohiko Fukuoka, et al.

It is certified that error appears in the above-identified patent and that said Letters Patent is hereby corrected as shown below:

Col. 10, line 4:  after "-N-oxide," insert -- 150 ml of toluene, 50 ml of isopropyl alcohol (IPA), --.

Signed and Sealed this

Twenty-third Day of November, 1993

Attest:

BRUCE LEHMAN

*Attesting Officer*  *Commissioner of Patents and Trademarks*